(12) United States Patent
BelBruno (10) Patent No.: US 11,567,049 B2
(45) Date of Patent: Jan. 31, 2023

(54) MOLECULARLY IMPRINTED POLYMER SENSORS

(71) Applicant: FreshAir Sensor, LLC, Lebanon, NH (US)

(72) Inventor: Joseph J. BelBruno, Hanover, NH (US)

(73) Assignee: FRESHAIR SENSOR, LLC, Lebanon, NH (US)

( * ) Notice: Subject to any disclaimer, the term of this patent is extended or adjusted under 35 U.S.C. 154(b) by 144 days.

(21) Appl. No.: 16/833,953

(22) Filed: Mar. 30, 2020

(65) Prior Publication Data
US 2020/0225202 A1   Jul. 16, 2020

Related U.S. Application Data

(63) Continuation of application No. 14/624,813, filed on Feb. 18, 2015, now abandoned.

(60) Provisional application No. 61/944,201, filed on Feb. 25, 2014.

(51) Int. Cl.
*G01N 33/00* (2006.01)

(52) U.S. Cl.
CPC ................ *G01N 33/0047* (2013.01)

(58) Field of Classification Search
CPC .................................. G01N 33/0047
See application file for complete search history.

(56) References Cited

U.S. PATENT DOCUMENTS

| | | | |
|---|---|---|---|
| 4,314,027 A | 2/1982 | Stahr | |
| 6,484,560 B1 | 11/2002 | Prest | |
| 6,670,427 B1 | 12/2003 | Ulbricht | |
| 6,787,350 B2 | 9/2004 | Bigelow, Jr. | |
| 6,798,220 B1 | 9/2004 | Flanigan et al. | |
| 7,291,465 B2 | 11/2007 | Karaolis | |
| 8,829,062 B1 | 9/2014 | Minko | |
| 2003/0129618 A1 | 7/2003 | Moronne et al. | |
| 2004/0126814 A1 | 7/2004 | Singh | |
| 2006/0041099 A1 | 2/2006 | Cernohous et al. | |
| 2007/0141683 A1* | 6/2007 | Warner | G01N 33/0047 435/128 |
| 2008/0144002 A1* | 6/2008 | Murray | G01N 21/00 356/36 |
| 2008/0286830 A1 | 11/2008 | Scatter et al. | |

(Continued)

FOREIGN PATENT DOCUMENTS

| | | |
|---|---|---|
| WO | WO 2008/045596 | 4/2008 |
| WO | WO 2011/058308 | 5/2011 |
| WO | WO 2014/030002 | 8/2013 |

(Continued)

OTHER PUBLICATIONS

Fu et al., "Quartz Crystal Microbalance Sensor for Organic Vapor Detection Based on Molecularly Imprinted Polymers", Anal. Chem., 2003, 75, pp. 5387-5393.

(Continued)

*Primary Examiner* — Lyle Alexander
*Assistant Examiner* — Dwan A Gerido
(74) *Attorney, Agent, or Firm* — Lathrop GPM LLP (57) ABSTRACT

Systems and methods for the detection of one or more target molecules, such as benzene, are described. The systems and methods may include a molecularly imprinted polymer film; a sensing material, wherein the molecularly imprinted polymer film comprises a polymer host with one or more binding sites for one or more target molecules. The molecularly imprinted polymer film may be coated upon the sensing material.

14 Claims, 4 Drawing Sheets

(56) References Cited

U.S. PATENT DOCUMENTS

| | | |
|---|---|---|
| 2009/0325147 A1 | 12/2009 | Jones, Jr. |
| 2010/0068820 A1 | 3/2010 | Meathrel et al. |
| 2010/0311181 A1 | 12/2010 | Abraham et al. |
| 2011/0054132 A1 | 3/2011 | Yiannikouris et al. |
| 2011/0143962 A1 | 6/2011 | Chaubron |
| 2014/0242237 A1* | 8/2014 | Belbruno ............. C08L 33/12 426/422 |
| 2014/0242601 A1 | 8/2014 | Belbruno |

FOREIGN PATENT DOCUMENTS

| | | |
|---|---|---|
| WO | WO 2014/070727 | 5/2014 |
| WO | WO 2015/130529 | 9/2015 |

OTHER PUBLICATIONS

International Search Report and Written Opinion in corresponding International Application No. PCT/US2015/016373, dated Jul. 21, 2015, 10 pages.

International Search Report and Written Opinion in corresponding International Application No. PCT/US2013/067246, dated Mar. 20, 2014, 12 pages.

Meruva et al., "Rapid identification of microbial VOCs from tobacco molds using closed-loop stripping and gas chromatography/time-of-flight mass spectrometry," J Ind Microbial Biotechnol, 2004: 31, DD. 482-488.

Moularat et al., "Detection of fungal development in closed spaces through the determination of specific chemical targets," Chemosphere 72, 2008, pp. 224-232.

U.S. Appl. No. 14/065,990, Office Action dated Jun. 23, 2016 in the U.S. Patent and Trademark Office.

U.S. Appl. No. 14/065,990, Reguirementfor Restriction/Election dated Apr. 1, 2016 in the U.S. Patent and Trademark Office.

Yoon et al., "Colorimetric Sensors for Volatile Organic Compounds (VOCs) Based on Conjugated Polymer-Embedded Electrospun Fibers," J. Am. Chem. Soc. 2007: 129, pp. 3038-3039.

* cited by examiner

MOLECULARLY IMPRINTED POLYMER SENSORS

CROSS-REFERENCE TO RELATED APPLICATIONS

This application is a continuation of U.S. patent application Ser. No. 14/624,813, filed Feb. 18, 2015, which claims priority to U.S. Provisional Patent Application No. 61/994,201, filed Feb. 25, 2014; the contents of which are hereby incorporated by reference in their entirety.

FIELD OF THE INVENTION

The present invention relates to systems and methods for passive sensors, and, more specifically, to systems and methods for molecularly imprinted polymer-based sensors for detecting target molecules, for example, small aromatic molecules, such as, for example, benzene.

BACKGROUND OF THE INVENTION

Molecular imprinting is a technique to produce molecule specific receptors analogous to those receptor binding sites in biochemical systems. A molecularly imprinted polymer (MIP) is a polymer that is formed in the presence of a template or target analyte molecule producing a complementary cavity that is left behind in the MIP when the template is removed. The MIP demonstrates affinity for the original template molecule over other related and analogous molecules.

Most MW materials are based on non-covalent interactions, most notably hydrogen bonding or electrostatic forces. Small aromatic molecules, such as benzene, being non-polar, may not present such opportunities for interaction with the polymer host. Although considerably weaker interactions than hydrogen bonding, $\pi$-$\pi$ interactions or hydrophobic interactions are available to enhance the always present shape recognition (via van der Waals forces; as used herein, van der Waals forces are intended to include both dispersion forces and dipole-dipole interactions) of MW cavity binding sites.

SUMMARY OF THE INVENTION

Embodiments of the present invention solve many of the problems and/or overcome many of the drawbacks and disadvantages of the prior art by providing systems and methods for molecularly imprinted polymer-based sensors. This disclosure relates to the field of molecularly imprinted polymers (MIP), and in certain embodiments relates to passive sensors based on MW films to detect small aromatic molecules, such as benzene.

Certain embodiments may include systems and methods for detecting small aromatic molecules using molecularly imprinted polymers. The systems and methods may include a molecularly imprinted polymer film; a resistive or capacitive material, wherein the molecularly imprinted polymer film comprises a polymer host with one or more binding sites for one or more target molecules. The molecularly imprinted polymer film may be coated upon the resistive or capacitive material.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE PREFERRED EMBODIMENTS

Systems and methods are described for molecularly imprinted polymer-based sensors. In certain embodiments, the tools and procedures may be used in conjunction with detection of aromatic molecules. Aromatic molecules may be any organic molecules. In certain embodiments, aromatic molecules may be organic molecules with planar rings having $4n+2\pi$-electrons, where n=0, 1, 2, etc. In certain embodiments, the detection is of small aromatic molecules that may be non-polar. In certain embodiments, small molecules may be those that are less than approximately 400 amu based on molecular weight. In certain embodiments, small molecules may be planar ring systems where the number of fused rings is fifty or less, forty or less, thirty or less, twenty or less, fifteen or less, ten or less, five or less, four or less, three or less, or two or less. In certain embodiments, the small aromatic molecules may be benzene. The examples described herein relate to benzene and its derivatives for illustrative purposes only. The systems and methods described herein may be used for many different industries and purposes, including detection of any non-polar molecules, detection of other classes of molecules, and/or other industries completely. In particular, the systems and methods may be used for any industry or purpose where molecularly imprinted polymer-based sensors are useful.

Molecularly Imprinted Polymer (MIP) Films and Sensors

Embodiments described herein may provide systems and methods for producing MIPs. The polymer of an MIP may contain one or more binding sites for one or more target molecules. Without being bound by any particular theory, it is believed that the target molecule may bind to the binding sites in the polymer layer via physical or chemical forces such as hydrogen bonding, $\pi$-$\pi$ interactions, hydrophobic interactions, electrostatic interactions, van der Waals forces, ionic bonds or even covalent bonds. The binding can also include combinations of these forces, especially when large heterocyclic hydrocarbons are the target. The polymer layer of the MIP may also be referred to as the polymer host. The polymer layer (polymer host) of the MIP may contain a structural polymer component (structural component) and a reporting polymer component (reporting component). The structural component of the polymer layer may provide structural support for the polymer layer of the MW. In certain embodiments, the structural component primarily forms the binding site of the polymer host. In certain embodiments, the reporting component of the polymer host is a material that allows for detection of rebinding. Rebinding may refer to incorporation of a target molecule into an empty MW cavity from an analytical sample. The detecting material may be resistive, capacitive, or strain sensitive material.

In certain embodiments, a change in a property associated of the polymer host may indicate the presence of a target molecule in a MIP film. The absence of a change may indicate the absence of a target molecule in a MW film. In certain embodiments, a change in resistance, capacitance, or strain of the polymer host may indicate presence of a target molecule. The change may be an alteration in any measurable property of the polymer host. In certain embodiments, the change may be a change in electrical resistance or conductivity. In certain embodiments, the change may be a change in color or other visual indication. The MIP may be coated onto an electrode and a change in the resistance of the polymer between the adsorbed and desorbed state may be used to detect a target molecule. Alternatively, a capacitor may be constructed with the MIP as a dielectric between two electrodes. In certain embodiments, the bottom electrode may be solid, the MIP may be a next layer, and then an electrode may be adjacent the MIP, where the electrode that has one or more gaps that may allow vapor to pass through. Changes in capacitance in the presence and absence of target molecules may be measured.

As used herein, a film generally refers to a coating of a surface. In alternate embodiments, a film may be a thin layer of material that is not coated on another surface. An embodiment of a film may be coating of a surface by a polymer or MIP. In one embodiment, a MW film may be from about 1 nm to about 100 μm in thickness. In certain embodiments, the MIP film may be from about 100 nm to about 500 nm in thickness. In certain embodiments, the MW film may allow the changes in adsorption to influence the reporting component and report an outcome. In general, MIP film sensor functionality may depend upon detecting differences in a property of the MW film, such as capacitance, resistance, or color of the MW film, as a function of the adsorption of a target molecule. In certain embodiments, MIP film sensors can be tested for their ability to detect target molecules by using various vapor chambers or otherwise exposing the MW film sensors disclosed herein to samples of various gases.

MIP polymers may include, but are not limited to, polymethylmethacrylate (PMMA), polystyrene (PS) and similar compounds. Depending upon the MIP polymers of choice, the solvents in which the MIPs have high solubility can include, but are not limited to, aromatic hydrocarbons and chlorinated hydrocarbons. For example, benzene may be compatible with the polymers and a chlorinated solvent could be used as the porogen in phase inversion production, since the boiling points of $CH_2Cl_2$ and $CHCl_3$ are 40° C. and 20° C. below that of benzene (Tb=81° C.), respectively. It will be appreciated by those skilled in the art that modification of polymers and/or solvents may allow for tuning the process of producing MIPs to the chemistry of a target molecule.

In certain embodiments, target molecules may include benzene, benzene derivatives, and combinations thereof. Benzene derivatives may include, but are not limited to, toluene and xylene. In some embodiments, heterocyclic hydrocarbons represent the target molecules.

In some embodiments of the MIPs disclosed herein, homologous molecules, homologs, of the target molecule can be used instead of the target molecule to produce MIPs that detect the target molecule. Homologs of target molecules may include molecules that are similar to the target molecule in various attributes including, but not limited to, size, electrostatic potentials, electronegativity, charge density, chemical bonding potential, and molecules that have similar shapes to the target molecule. Homologs may include isomers and stereoisomers of the target molecule.

In an embodiment, MIP films can be regenerated by extracting and/or evaporating target molecules from a MIP film by soaking or washing in a solvent in which the polymer host is insoluble, but the target molecule is soluble. In an embodiment, the target molecules can be removed from the MIP binding sites through extraction and/or evaporation processes. The MIP films may then be washed and dried to allow the solvent and the target molecule to be separated from the MIP films. After extraction and/or evaporation of the target molecule, the MIP films may be ready to detect target molecules again. If the target molecules of interest are charged, the films may be regenerated by charging or reversing the charge on the MIP film.

Strain measurements, such as color changes, of embodiments of the sensors presented herein may be indicative of the binding of target molecules. Additional evidence of target molecules being bound in the MIP layer can be obtained through IR spectroscopy and gas chromatographic experiments.

The morphology of MIP films disclosed herein can be further characterized by scanning electron microscopy.

Methods of Making MIP Films and Sensors

Systems and methods are described for making MIPs and sensors that use MIPs. In an embodiment, MIPs may be made by mixing together a structural component, a reporting component, a target molecule and a first solvent. In certain embodiments, the structural component and the target molecule may be mixed into the solvent with a later addition of the reporting component. Various orders of addition and mixing may be used. In an embodiment, a structural component may be a structural polymer. In an embodiment, a reporting component may be a reporting polymer. In an embodiment, the solution of the polymer components, the first solvent, and the target molecule may be a molecularly imprinted polymer solution. The molecularly imprinted polymer solution can then be coated onto a surface and allowed to dry. Coating may be by spin coating, dip coating, drop casting, or other coating techniques. When the molecularly imprinted polymer solution is drying, the polymers may form the binding sites for the dissolved target molecules as the polymer layer polymerizes around the target molecules. Next, the target molecules may be selectively removed from the MW layer by either evaporation of the target molecule or through extraction with a solvent that selectively dissolves the target molecule, but does not dissolve the polymer host.

The solvent used in making the MIPs can boil at a lower temperature than the target molecule. This may allow the target molecules to form recognition sites during spin or dip coating. A solvent can then be used to remove the target molecules. The solvent should be incompatible with the polymer host to promote precipitation of the MW. Alternatively, the target molecule or template can be evaporated from the MIP if the solvent has a lower boiling point than the target molecule or template.

There are various techniques for producing films including phase inversion and synthesis of MIPs using monomers with crosslinking agents. In certain embodiments of the present disclosure, films may be employed to directly measure the target concentration in concert with a second polymer included in composite materials to improve the porosity of the film. In certain embodiments, films may change color, such as from blue to red or any other detectable color change, when it is subjected to increased strain due to, for example, the binding of the target molecule.

In an embodiment, the sensor may be a device that simultaneously monitors target molecules, such as small aromatic molecules. In certain embodiments, the sensor may monitor benzene. In certain embodiments, the device may simultaneously monitor any combination of various molecules. In an embodiment, the sensor may be read visually. In another embodiment, the sensor may be coupled to electronics that read the MIPs and report wirelessly to a central facility. Alternatively, the sensor may be incorporated into a portable and/or handheld device for measurement and processing onsite. The polymer host and the MW synthesis for each component may be determined by the physical and/or chemical characteristics of the targeted molecules. Each MIP within a sensor, such as a test strip, may be specific to a single target molecule. In an embodiment, the reporting aspect of the sensors may be based on a physical property change from a first state to a second, different state upon reinsertion of the target molecule into the MIP.

The structural polymer may include, but is not limited to, polymethylmethacrylate (PMMA), polystyrene (PS), and combinations thereof. Other structural polymers may be used. MIP production is typically, but not limited to, a ratio of approximately 1 g of structural polymer dissolved in approximately 10 mL of solvent with approximately 0.3 g of the target molecule. Target molecule can range from about 1 to about 10%, preferably in the range from about 3 to about 5%. In certain embodiments, the polymer is not greater than about 10% and may be between about 3 to about 10%. The mixture may be precipitated to produce the solid MIP. Precipitation may include spin coating or drop casting or formation of nano- or microspheres.

The reporting layer of the sensor, such as a resistance, capacitance, or color reporting layer, may be produced by any standard polymerization methods known to one of skill in the art. The MIP may then be applied to this polymerized reporting layer. The MIP could also be formed to incorporate antibodies to molecules that could then be used to detect the antigen that bound to the antibody. Similarly, the MIP could incorporate antigens to permit them to detect antibodies or antibody conjugates.

Embodiments of MIP Films and Sensors

Most MW materials are based on non-covalent interactions, most notably hydrogen bonding or electrostatic forces. Benzene, for instance, being non-polar, does not present such opportunities for interaction with the polymer host. Although considerably weaker interactions than hydrogen bonding, 7E-7E interactions or hydrophobic interactions may enhance the always present shape recognition (via van der Waals forces) of the MIP cavity binding sites. Certain embodiments may utilize the unexpected ability to use MIP sensors to detect non-polar molecules, such as benzene. Polymethylmethacrylate (PMMA) may be useful for shape recognition MIPs and polystyrene (PS) may provide both shape recognition and weak template-host interaction. Both polymers are soluble in aromatic hydrocarbons and chlorinated hydrocarbons. As such, benzene may be chemically compatible with the polymers and a chlorinated solvent may be used as the porogen in phase inversion production, since the boiling points of $CH_2Cl_2$ and $CHCl_3$ are 40° C. and 20° C. below that of benzene ($T_b$=81° C.), respectively.

MIPs disclosed herein may be used for sensing. Polymers employed in the production of MIPs disclosed herein are also referred to as polymer hosts. Molecules disclosed herein for the production of the cavities in the MIPs are referred to interchangeably as templates, targets, or target molecules.

Embodiments described herein may provide systems and methods to produce sensors that incorporate a reporting MIP film. The methods may involve using the target molecules in the preparation of the MIP films and sensors comprising MW films.

When the target molecule is removed, it may leave behind a MIP with cavities complementary in shape and functionality to the target molecule, which can rebind, in the cavities, a target identical to the original target molecule. Embodiments may employ phase inversion type MIP production as well as synthesis of MIPs using monomers with crosslinking agents. Both systems can be employed for the product.

Phase Inversion MIPs.

Films of MIP may be deposited on a substrate. Exemplary substrates may include, but are not limited to, mica, quartz, silicon, any plastic such as polycarbonate, polystyrene, etc. The MIP may be deposited using various techniques. Deposition techniques may include, but are not limited to dip coating, knife edge coating, and/or spin coating to produce an even, reproducibly thin film. In the case of PMMA, the polymer may first be dissolved. The PMMA may be dissolved in, for example, $CHCl_3$, which may be both the solvent and porogen. Post-dissolution, a target molecule, such as benzene, may be added. The solution may be stirred, by mechanical or other methods. The stifling may be for various time periods depending on the desired result, but may be from approximately 6 hours to approximately 24 hours, from approximately 8 hours to approximately 20 hours, or from approximately 10 hours to approximately 16 hours. In certain embodiments, the stirring is for approximately 12 hours. The stirring may be performed in a sealed container to establish the MIP network in solution. In certain embodiments, the stirring can be at room temperature or even higher or lower temperatures. These temperatures may be dictated by the solvent choice. Utilizing temperature may enhance the strength of certain forces, such as van der Waals forces, over the forces created by the vibrating molecules.

The ratio of compounds may vary. As an example, the ratio of PMMA to benzene to chloroform may vary. The weight of polymer may be in the range of approximately 3%-approximately 15% of the porogen by weight. The template is typically in the range of approximately 3%-approximately 5% of the porogen by weight. Required coating speed may be estimated based on the MIP solution viscosity. In certain embodiments, a bulk material may be produced by precipitating the polymer by addition to the MIP solution of a poor solvent, such as water.

Qualitative testing of the success of the procedure may be accomplished by attenuated total reflection IR spectroscopy. Spectra may be examined for the 'as produced' film, the template may be extracted either by evaporation or by solvent extraction with n-hexane to measure the 'extracted' MIP and then a vapor phase reinsertion may be attempted to record the 'reinserted' spectrum. The room temperature vapor pressure of benzene may be sufficient for this reinsertion experiment. Polystyrene MIPs may be produced with the same protocol and the same solvents. The PMMA-MIP may be a pure shape recognition polymer; the PS-MW may add a weak chemical recognition element via 7E-7E interactions to the shape recognition feature.

In certain embodiments, a conductive film may be used as the polymer host. In this case the polymer may be poly-3-methylthiophene, soluble in $CHCl_3$. The addition of the benzene template may create binding sites when the solution is deposited using a spin coater.

MIP Synthesis.

MIPs are normally synthesized in producing bulk material. Synthesis may be used in this application for sensors because the synthesis may provide a readily varied concentration of crosslinking agent. Crosslinking may provide more rigid binding cavities. In certain embodiments, to produce films, partially reacted solutions may be used, which may be deposited via spin coating. The spin copolymerization process of the film may be completed using a lamp, such as an Hg lamp. In synthesis, the functional monomer, for example, methylmethacrylate, may be mixed in solution with $CHCl_3$. Benzene template may be added. The solution may be allowed to mix so that the functional monomer and template interact. After a predetermined mixing time, such as up to approximately six hours, or approximately 1-approximately 2 hours, the crosslinking monomer, for example, ethylene dimethacrylate, may be added and the new solution may be stirred for approximately 30 minutes. The solution may be de-oxygenated by flowing a gas through the mixture by reducing ambient pressure or by increasing the temperature, all within the skill of those in the art. The gas may be, but is not limited to, nitrogen, argon, etc. A polymerization initiator may be added. The polymerization initiator may be, for example, azobisisobutyronitrile (AIBN) may be added. The solution may be heated to approximately 55° C.-approximately 75° C. In certain embodiments the solution may be heated to approximately 70° C., a temperature less than the boiling temperature of the target molecule, benzene. In certain embodiments, the solution may be heated to a temperature less than approximately 5° C.-approximately 10° C. below the porogen boiling point. The polymer may precipitate out of solution as it is formed. The precipitate may be collected after a set time, such as between approximately 3-approximately 24 hours, or after approximately five hours. The template may be extracted and cleansed of any remaining monomers. Using SPE, MW effectiveness may be tested as noted above. In certain embodiments, a ratio of approximately 6:1:1 (crosslinker:functional monomer:template) may be effective. Again, the use of styrene as the functional monomer may follow analogously.

Sensors

Chemiresistors may be produced as target molecule sensors, regardless of the chemistry used in the MW production. As such, sensors may be built on interdigitated electrodes. These sensors may be approximately 20 mm×approximately 20 mm with approximately 316 interdigitated fingers of approximately 40 μm width and spaced approximately 20 μm apart. The electrodes may be coated with the appropriate MIP film.

For poly-3-methylthiophene, the process of producing sensors may include dissolving approximately 5% by weight of poly-3-mehtylthiophene in chloroform and stifling until fully dissolved. The process may then involve mixing approximately 1%-approximately 5% benzene into the solution and stifling for approximately 6-approximately 24 hours to develop the network. Approximately 2000 μL of the solution described in the above production techniques may be deposited on the electrodes and placed in a spin coater. After spinning, the coating may be approximately 300-approximately 500 nm thick. Polythiophene may be either p-doped or n-doped. The presence of benzene may inject electrons into the film and increase its conductivity. Adsorption may be detected and used to calibrate the device by measuring the resistance across the electrodes as a function of the concentration of benzene in the nascent atmosphere. The sensor may be easily recycled as the benzene desorbs and evaporates from the film.

Using either PS or PMMA, both non-conducting, as the host polymer may preclude a direct electrical response due to the presence of benzene. The use of single-walled carbon nanotubes (SWCNTs) as the conductive element across the interdigitated electrodes may be used. In this procedure, the SWCNTs may be coated with the imprinted polymer. The nanotubes may reflect the changes in the MIP (charge is either injected into the nanotubes or removed from it) by changing the resistance across the electrodes. This protocol may allow use of non-conducting polymers, as is required for the non-polar benzene template, but still maintain a chemiresistive element.

Sensor films may be used in the microcontroller driven sensing circuitry for both personnel sensors and room-based sensors or may be used as an inserted sensor in any other hand held device used to sample a particular atmosphere or occupied space.

Figure 1:
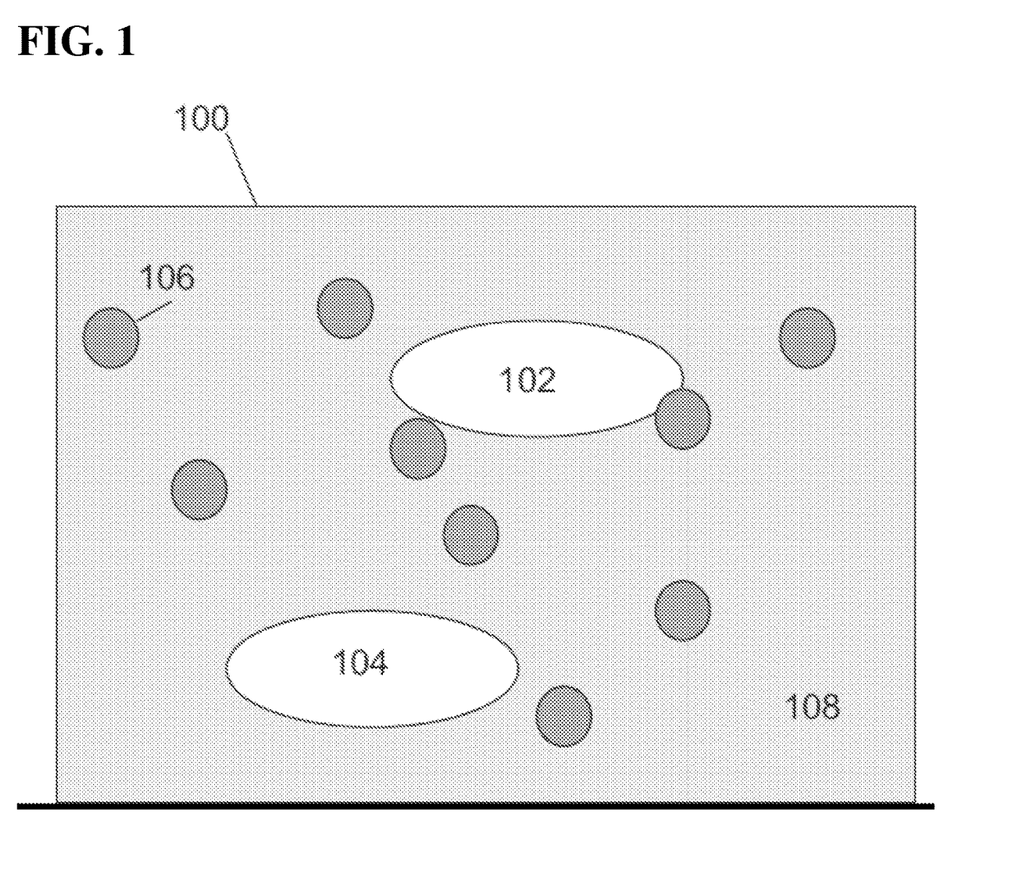
FIG. 1 shows an exemplary, simplified molecularly imprinted polymer solution prior to film deposition according to one embodiment.

FIG. 1 illustrates an embodiment of a simplified molecularly imprinted polymer solution. A molecularly imprinted polymer solution 100 may include structural components 102, 104 dissolved in a solvent 108. The polymer solution 100 may also include one or more target molecules 106 dissolved in the solvent 108. As illustrated in FIG. 1, a target molecule 106 may be bonded to the structural component 102 in the polymer solution 100, also referred to as the MIP solution.

The interaction between a polymer host and a target molecule in a MIP can involve associations between the polymer host and the target molecule. The binding interaction can exploit other various forces in conjunction with shape recognition, but the interaction between polymer host and the target molecule can include any interactions between the target molecule and the polymer host.

When the target molecule is removed via extraction or evaporation or by other removal means, it may leave behind a MIP with cavities that are complementary in shape to the target molecule and act as a binding site to the target molecule or similar molecules. The MIP films disclosed herein may be capable of rebinding target molecules through subsequent rounds of use when the MIP is regenerated between measurements by removing the target molecule from the MIP before the next use of the MIP film and/or sensor.

In another embodiment, MIPs can be produced by dissolving the polymer or polymer host components, i.e., reporting and structural, and target molecules in a first solvent to form a molecularly imprinted polymer solution. In one embodiment, the target molecule may form between about 1 and about 30 weight percent of the molecularly imprinted polymer solution. In a certain embodiments, the target molecule may form between about 2 and about 20 weight percent of the molecularly imprinted polymer solution. In certain embodiments, the target molecule may form between about 2 and about 15 weight percent of the molecularly imprinted polymer solution.

In an embodiment of a MIP of the present disclosure, the molecularly imprinted polymer solution has a molar ratio of from about 10:1 to about 1:1 to about 1:10 of the structural component to the reporting component. In an embodiment, the molecularly imprinted polymer solution may be from about 1 to about 30 percent of the target molecule or homolog by weight. In a certain embodiment of a MIP of the present disclosure, the molecularly imprinted polymer solution may have a molar ratio of from about 5:1 to about 1:1 to about 1:5 of the structural component to the reporting component. In a certain embodiment, the molecularly imprinted polymer solution may be from about 2 to about 20 percent of the target molecule or homolog by weight. In a certain embodiment of a MIP of the present disclosure, the molecularly imprinted polymer solution may have a molar ratio of from about 1:1 of the structural component to the reporting component. In a certain embodiment, the molecularly imprinted polymer solution may be from about 2 to about 10 percent of the target molecule or homolog by weight.

Figure 2A:
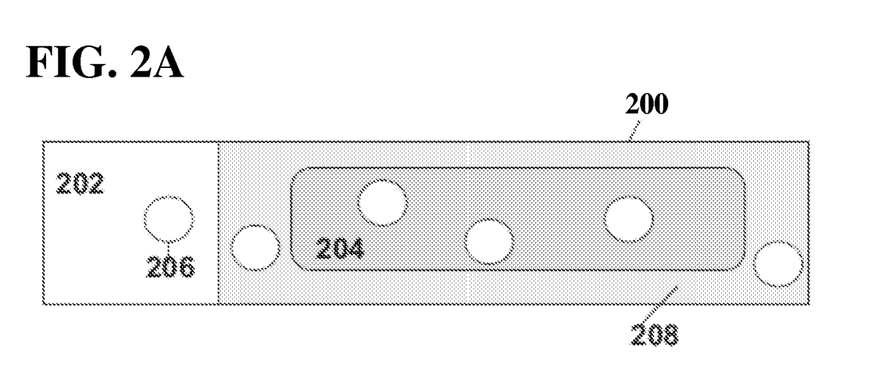
FIG. 2A shows an exemplary test strip for small aromatic molecules according to one embodiment.

FIG. 2A illustrates an exemplary test strip 200 that may include a plastic substrate 202 coated with coating 208. A portion of the coated plastic substrate may be covered with MW film 204. A sample solution 206 can be deposited on MIP film 204 and followed by washing sample solution. When a target molecule binds to the MW film 204, the test strip may change, to indicate a "Yes" for the presence of the target. Otherwise, if no target molecule binds to the MIP film 204, there may be no change, which indicates "No" for the presence of the target. Color, resistance and/or capacitance indicators may be provided by the sensor.

Figure 2B:
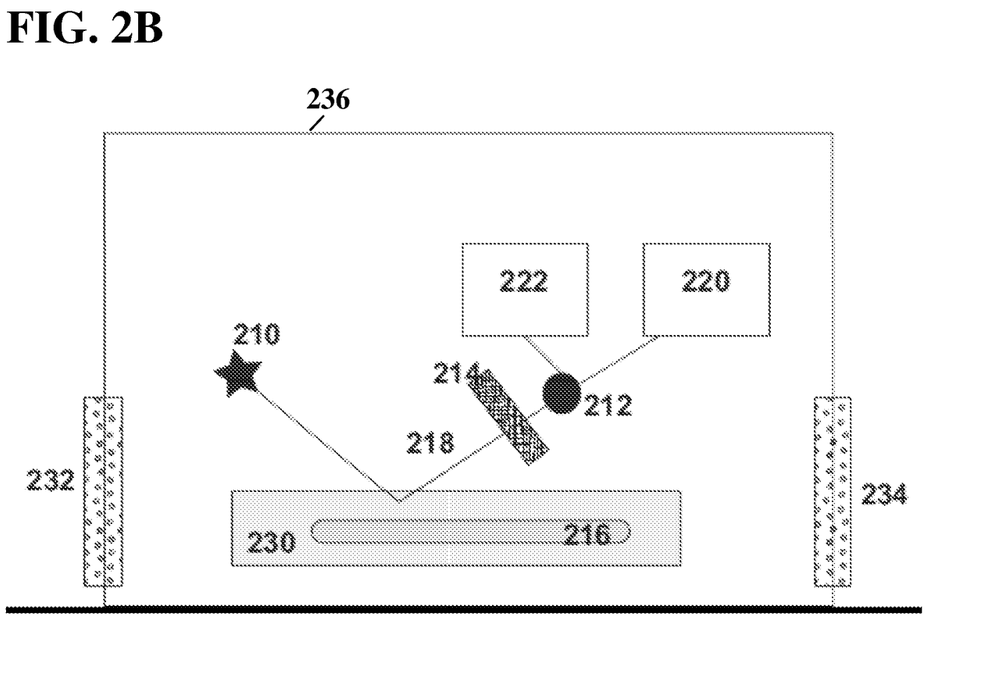
FIG. 2B shows a system with electronic reading of a sensing strip according to one embodiment.

FIG. 2B illustrates a system with electronic reading of the sensing strips and local alarm plus wireless reporting of the results obtained as described in FIG. 2A. The electronic reader may include one or more light emitting diodes 210 or other light sources and one or more detectors 212 to receive light reflected off the MIP. One or more filters 214 may admit only light reflected from the coating 216. When the coating, due to adsorption of the target into the MW, changes, a reflected light signal 218 may diminish and/or disappear and a local alarm 220 may be triggered. Reflected light signal 218 may reflect off MIP 216 and/or coating 208. Alternatively or in addition, a wireless signal 222 may be sent with a notification is sent to a remote location. The signal may be sent wirelessly or via any other data network. The notification may be one or more of an SMS message, MMS message, email, fax, phone call, etc. One or more airflow screens 232 may be provided to allow air into a housing 236. One or more fans 234 may be provided to draw air through the housing 236. In certain embodiments, both elements 232 and 234 may be screens or fans depending on the desired operation.

Figure 3:
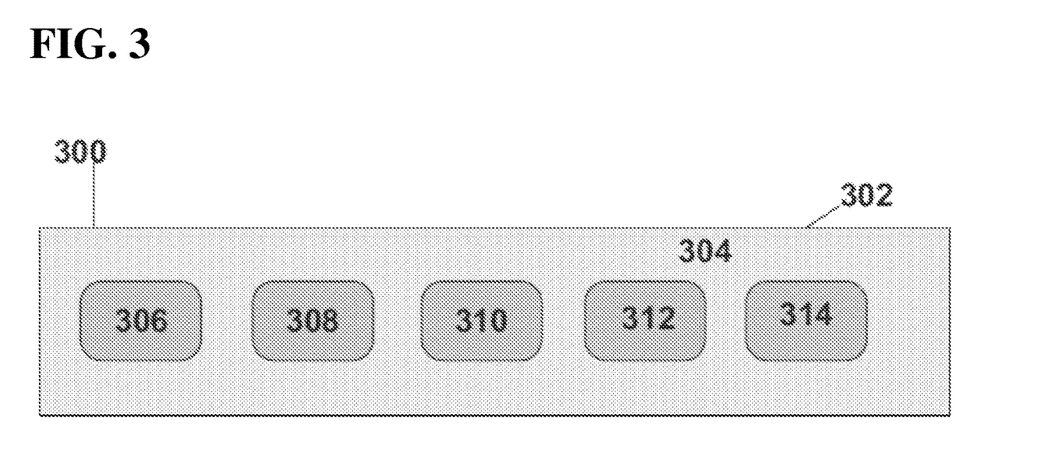
FIG. 3 illustrates an exemplary multicomponent test strip according to one embodiment.

FIG. 3 illustrates an exemplary multi-band test strip 300. The multi-band test strip 300 may include a plastic substrate 302 covered with a reporting coating layer 304 isolated into five different regions. Each region may have a MIP solution 306, 308, 310, 312, 314 targeted to a different target molecules deposited onto the coating reporting polymer. Alternatively, each region may be targeted to the same target molecule as a redundant test. If a particular target is present and is adsorbed by its respective MIP, the adsorption event may trigger a change in the reporting layer, which may provide an indication of the presence of the target. Otherwise, no change may occur in each region. One of the benefits of the methods disclosed herein over conventional methods for detection of the target molecule may be molecular specificity. The sensor may be passive, because the target molecules may be adsorbed by the MW film by exposure. There may be no need for the use of a pump or other moving parts for actively drawing air into the device although an additional embodiment may include, for example, a fan to draw air over the sensor.

Figure 4:
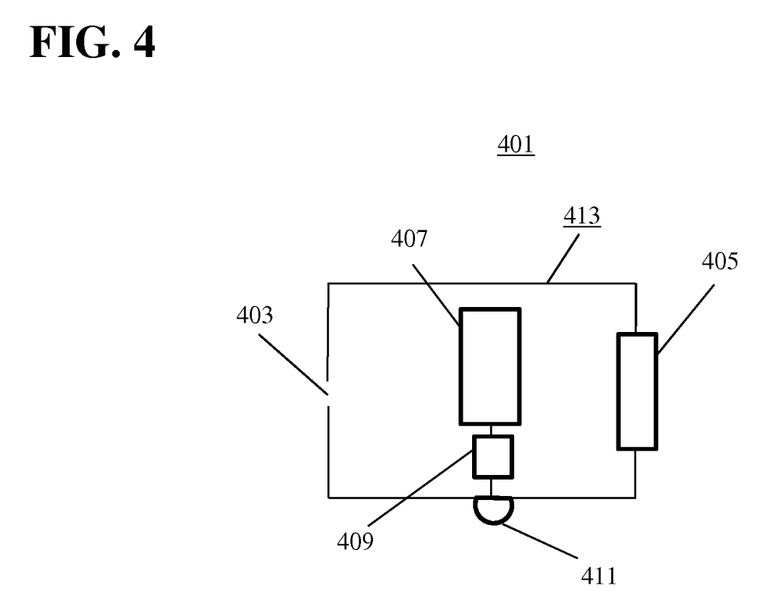
FIG. 4 shows an exemplary device for detecting small aromatic molecules according to one embodiment.

FIG. 4 illustrates a system 401 for sampling target molecules. An inlet 403 may pass into a structural element. The inlet 403 may be fluidly connected to a housing 413. The inlet 403 may be an air inlet. The housing 413 may contain one or more fans 405. The one or more fans may draw air through the inlet 403 and/or housing 413. One or more MIP sensors 407 may be located within the housing 413. The housing 413 may at least partially surround the one or more MIP sensors 407. The one or more sensors 407 may be in communication with one or more signal processors 409 for determining the presence or absence of a target molecule based on measurements of the one or more MIP sensors 407. The one or more signal processors 409 may output a result, such as to an indicator 411. The indicator 411 may be one or more LED lights, a display, etc. coupled to the housing 413. Alternatively, or in addition, the output may be provided to a remote system via a wireless or wired connection for further processing, alerting, reporting, etc.

Embodiments described herein may fill an unmet need, as there currently exists no passive sensor for the real-time detection of small aromatic molecules, such as benzene. It will be appreciated by those skilled in the art that configuration, shape, and dimensions of the sensor can vary for particular applications.

Having described several embodiments, it will be recognized by those skilled in the art that various modifications, alternative constructions, and equivalents can be used without departing from the spirit of the disclosure. Accordingly, the above description should not be taken as limiting the scope of the disclosure. Those skilled in the art will appreciate that the presently disclosed instrumentalities teach by way of example and not by limitation. Therefore, the matter contained in the above description or shown in the accompanying drawings should be interpreted as illustrative and not in a limiting sense.

The following claims are intended to cover all generic and specific features described herein. Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A system for the detection of benzene, the system comprising:
   a polymer film molecularly imprinted with a template molecule to form cavities complementary in shape to benzene, each of the cavities forming a binding site specific for benzene;
   a sensing material for detecting binding of benzene to the polymer film, the polymer film being coated upon the sensing material, wherein the template molecule is benzene.

2. The system of claim 1, the sensing material being configured to exhibit change in resistance or capacitance upon binding of benzene to the polymer film.

3. The system of claim 1, wherein the polymer film is synthesized using monomers and crosslinking agents.

4. A method for producing a molecularly imprinted polymer film for detection of benzene, comprising:

dissolving a polymer, including a structural component and a reporting component, in a first solvent to form a first solution;

mixing a template molecule into the first solution to form a second solution, the template molecule being benzene;

coating the second solution onto a sensing material to form a first polymer film; and removing the template molecule from the first polymer film to form a molecularly imprinted polymer film.

5. The method of claim 4, the template molecule being benzene, the step of mixing comprising mixing benzene into the first solution.

6. The method of claim 4, the step of coating comprising spin coating, dip coating, knife edge coating, or drop casting the second solution onto the sensing material.

7. The method of claim 4, the step of removing comprising:

extracting the template molecule from the first polymer film using a second solvent that selectively dissolves the template molecule, but does not dissolve the polymer;

wherein the polymer is insoluble in the second solvent and the template molecule is soluble in the second solvent.

8. The method of claim 4, wherein the second solvent is n-hexane, an aromatic hydrocarbon, or a chlorinated hydrocarbon.

9. The method of claim 4, the first solvent having a boiling point lower than the boiling point of the template molecule, and the step of removing the template molecule comprising evaporating the template molecule from the first polymer film.

10. The method of claim 4, further comprising synthesizing the polymer using monomers and crosslinking agents.

11. A system for detecting benzene, the system comprising:

a polymer film molecularly imprinted with a template molecule to form cavities complementary in shape to benzene, each of the cavities forming a binding site specific for benzene, wherein the template molecule is benzene;

a sensing material for detecting binding of benzene to the polymer film, the polymer film being coated upon the sensing material;

a housing, the sensing material being located within the housing; and an inlet fluidly connected to the housing.

12. The system of claim 11, wherein the sensing material is in communication with one or more signal processors for determining the presence or absence of benzene based on measurements from the sensing material.

13. The system of claim 12, wherein the one or more signal processors output a result to an indicator.

14. The system of claim 12, wherein the measurement is a change in resistance or capacitance of the sensing material upon binding of benzene to the polymer film.

* * * * *